United States Patent [19]

Ducep et al.

[11] Patent Number: 5,145,861
[45] Date of Patent: Sep. 8, 1992

[54] FLUORINATED ARACHIDONIC ACID DERIVATIVES

[75] Inventors: Jean B. Ducep, Sundhoffen; Jean-Francois Nave, Strasbourg, both of France

[73] Assignee: Merrell Dow Pharmaceuticals Inc., Cincinnati, Ohio

[21] Appl. No.: 742,459

[22] Filed: Aug. 5, 1991

Related U.S. Application Data

[63] Continuation of Ser. No. 512,633, Apr. 18, 1990, abandoned, which is a continuation of Ser. No. 376,915, Jul. 5, 1989, abandoned, which is a continuation of Ser. No. 117,165, Nov. 4, 1987, abandoned.

[51] Int. Cl.$^5$ .............. A61K 31/41; A61K 31/22; C07D 257/04; C07C 67/36
[52] U.S. Cl. ................. 514/381; 514/549; 514/627; 548/250; 548/252; 560/204; 560/219; 564/201; 564/204
[58] Field of Search ............ 548/250, 252; 560/204, 560/219; 564/201, 204; 514/381, 549, 627

[56] References Cited

U.S. PATENT DOCUMENTS 3,057,893 10/1962 Smith, Jr. et al. ............... 541/381
4,670,465 6/1987 Guzman et al. ............... 514/522
4,708,964 11/1987 Allen ............... 541/381

FOREIGN PATENT DOCUMENTS 104468 4/1984 European Pat. Off. .
61-271246 1/1986 Japan .
12160 12/1986 Japan .
63-222143 1/1988 Japan .

OTHER PUBLICATIONS

Chemical and Pharmaceutical Bulletin, vol. 35, No. 4, 1987, pp. 1666–1669, Tokyo, JP; T. Taguchi et al.
Chemical Abstracts vol. 107, No. 7, Aug. 17, 1987, p. 685, abstract No. 58491e, Y. Kobayashi et al.
Chemical Abstracts vol. 109, No. 25, Dec. 19, 1988, p. 8222, abstract No. 230631e, Y. Kobayashi et al.
Chemical Abstracts vol. 108, No. 21, May 23, 1988, p. 675, abstract No. 186433v, Y. Kobayashi et al.
Pui-Yan Kwok, et al., Journal of the American Chemical Society 109, pp. 3692–3698, (1987).
Pui-Yan Kwok, et al., Journal of the American Chemical Society 109, pp. 3684–3692, (1987).
Stevenson, Paul Nelson, Novel Stragegies toward the Synthesis of 10,10–Difluoroarachidonic Acid, A dissertation approved Feb. 13, 1987.
Yoko Tanaka, et al., Archives of Biochemistry and Biophysics, vol. 263, No. 1, May 15, 1988, pp. 178–190.
Y. Kobayashi, L'Actualite Chimique, pp. 181–182, May, 1987.

*Primary Examiner*—Johann Richter
*Attorney, Agent, or Firm*—Stephen L. Nesbitt

[57] ABSTRACT

Fluorinated arachidonic derivatives are 5-lipoxygenase inhibitors which have the useful pharmacologic activity as antiallergy and anti-imflammatory agents and are useful for treating, for example, asthma, anaphylaxis, allergy, rheumatoid arthritis, and psoriasis.

27 Claims, No Drawings

FLUORINATED ARACHIDONIC ACID DERIVATIVES

CROSS-REFERENCE TO RELATED APPLICATION

This is a continuation of application Ser. No. 07/512,633, filed Apr. 18, 1990, now abandoned, which is a continuation of application Ser. No. 07/376,915, filed Jul. 5, 1989, now abandoned, which is a continuation of application Ser. No. 07/117,165, filed Nov. 4, 1987, now abandoned.

This invention relates to certain fluorinated arachidonic acid derivatives and their pharmaceutical uses.

BACKGROUND OF THE INVENTION

Lipoxygenases, which are found in various mammalian tissues including the lung, mast cells, platelets, and white cells, are enzymes which oxidize arachidonic acid into hydroperoxyeicosatetraenoic acids (HPETEs) which are in turn reduced to the corresponding hydroxyeicosatetraenoic acids (HETEs). The lipoxygenases are classified according to the position in the arachidonic acid which is oxygenated. Platelets metabolize arachidonic acid to 12-HETE via a 12-lipoxygenase, while polymorphonuclear leukocytes contain 5- and 15-lipoxygenases which oxidize arachidonic acid to 5-HPETE and 15-HPETE, respectively.

5-HPETE is the precursor of leukotriene $A_4$, an unstable precursor of two distinct groups of leukotrienes. The first of these are the peptido-lipid leukotrienes $LTC_4$ and $LTD_4$ formed sequentially by reaction of $LTA_4$ with glutathione followed by reaction with γ-glutamyl transpeptidase to form the cysteinyl-glycine adduct. These compounds account for the biologically active material known as the slow reacting substances of anaphylaxis (SRS-A).

These leukotrienes are potent smooth muscle contracting agents, particularly effective on smooth muscle but also on other tissues They also promote mucous production, modulate vascular permeability changes and are potent inflammatory agents in human skin. The leukotrienes are potent spasmogens of human trachea, bronchus and lung parenchymal strips. Administered as an aerosol to normal volunteers, leukotrienes have been found to be about 3800 times more potent than histamine itself. In vitro studies have shown that antigen challenge of human lung or human mast cells results in the production and release of significant amounts of leukotrienes. For these reasons leukotrienes are thought to be major contributors of the symptoms of asthma and anaphylaxis. The most important compound of the second group of leukotrienes is leukotriene $B_4$, a dihydroxy fatty acid. This compound is a potent chemotactic agent for neutrophils and in addition may modulate a number of other functions of these cells. It also affects other cell types such as lymphocytes and, for example, is thought to inhibit the phytohemagglutinin-induced elaboration of leukocyte inhibitory factor in T-lymphocytes. Leukotriene $B_4$ is also a potent hyperalgesic agent in vivo and can modulate vascular permeability changes through a neutrophil-dependent mechanism.

Psoriasis is a human skin disease which affects from about 2 to 6 per cent of the population but fully adequate therapy remains unavailable. One of the earliest events in the development of psoriatic lesions is the recruitment of leukocytes to the skin site. In human psoriatic skin, abnormally high levels of free arachidonic acid and lipoxygenase products are found. Among these, leukotriene $B_4$ has been identified in blister fluid from human psoriatic skin, and when injected into human skin, leukotriene $B_4$ induces a pronounced accumulation of neutrophils at the site of injection. Moreover in humans with stable psoriasis, intralesional injection of 15-(S)-HETE, an inhibitor of 5- and 12-lipoxygenases, produces considerable improvement of psoriatic plates.

The leukotrienes are important mediators of inflammatory diseases through their ability to modulate leukocyte and lymphocyte functions. The presence of the leukotrienes is thought to be responsible for many of the symptoms observed in allergy and rheumatoid arthritis patients.

Applicants have now discovered a novel class of fluorinated arachidonic acid derivatives which are potent inhibitors of 5-lipoxygenase, the enzyme responsible for the conversion of arachidonic acid to the leukotrienes. These new compounds are useful as antiallergic and anti-inflammatory agents in the treatment of asthma, anaphylaxis, allergy, rheumatoid arthritis, and psoriasis.

SUMMARY OF THE INVENTION

Fluorinated arachidonic derivatives of formula 1:

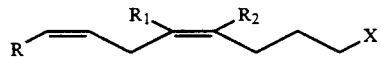

wherein each of
$R_1$ and $R_2$ are a hydrogen or a fluoro group with the proviso that at least one of $R_1$ and $R_2$ must be a fluoro group;
X is a C(O)OR' group wherein R' is a hydrogen, a straight chain $(C_1-C_6)$alkyl group, or
X is a group of the formula —C(O)OCH$_2$CH(OR")CH$_2$(OR''') wherein R" is a long chain fatty acid residue and wherein R''' is a hydrogen or a long chain fatty acid residue, or
X is a —C(O)NH$_2$ or —C(O)NH(OH) group, or
X is a 1H-tetrazol-5-yl group; and
R is a group of one of the structural formulae

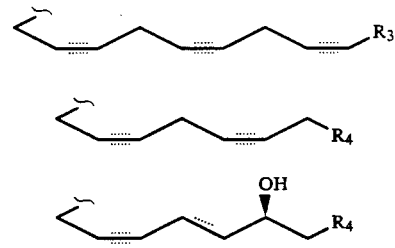

wherein $R_3$ is a hydrogen or a straight chain $(C_1-C_4)$alkyl and $R_4$ is a hydrogen or a straight chain $(C_1-C_6)$alkyl and wherein a dotted line indicates an optional double or triple bond as well as where X is C(O)OR' and R' is a hydrogen and the pharmaceutically acceptable salts thereof are 5-lipoxygenase inhibitors which have the useful pharmacologic activity as antiallergy and anti-inflammatory agents and are useful for treating, for example, asthma, anaphylaxis, allergy, rheumatoid arthritis, and psoriasis.

DETAILED DESCRIPTION OF THE INVENTION

The R groups of the compounds of this invention may contain one or more double bonds. The double bonds of the R groups of this invention must be of the Z or cis configuration except for the double bond at the 13,14 position of the hydroxylated R groups which must be of the trans or E configuration. Moreover the carbon atom to which the hydroxy group is attached in the hydroxylated R groups, the 15 carbon atom, is chiral. Of those compounds having a hydroxylated R group, applicants prefer those with the S configuration at the carbon atom bearing the hydroxy group.

As is true with many classes of pharmacologically active compounds, certain subclasses are preferred. In the compounds of this invention those of formula 1 wherein X is a CO₂H group and wherein X is a group of the formula —C(O)OCH₂CH(OR")CH₂(OR''') wherein R" is a long chain fatty acid residue and wherein R''' is a hydrogen or a long chain fatty acid residue are preferred. Also preferred are those compounds of formula 1 wherein the R group is hydroxylated, especially those hydroxylated R groups having two double bonds. Additionally preferred are those R groups wherein $R_3$ is an ethyl group, especially those having two or three double bonds and which correspond to 5,8,11,14-eicosatetraenoic acid and 5,8,11,14,17-eicosapentaenoic acid. Applicants prefer those compounds of formula 1 wherein $R_1$ is a fluorine and wherein $R_1$ and $R_2$ are both fluorines.

Those compounds of this invention wherein X is a group of the formula —C(O)OCH₂CH(OR")CH₂(OR''') are analogs of the naturally occuring arachidonic acid containing lipids from which arachidonic acid is released in mammals. The groups R" and R''' can be long chain, fatty acid residues. Suitable long chain, fatty acid residues are those of the naturally occuring saturated and unsaturated fatty acids as well as analogs of these naturally occuring fatty acids. The carbon chains of the naturally occuring fatty acids are usually unbranched, usually contain an even number of carbon atoms, and usually any double bonds are of the cis configuration. Additionally the double bonds of the naturally occuring unsaturated fatty acids are never conjugated. However, the long chain, fatty acids of this invention may be branched, may contain an odd number of carbon atoms, may contain conjugated double bonds, and may have trans configuration. Examples of suitable fatty acids are butyric, caproic, caprylic, capric, lauric, myristic, palmitic, stearic, arachidic, lignoceric, oleic, palmitoleic, linoleic, γ-linolenic, linolenic, arachidonic 5,8,11,14,17-eicosapentaenoic acids.

The compounds of this invention can be prepared by the condensation of the ylid of triphenylphosphonium bromide, 2 having $R_1$ and $R_2$ as defined above in formula 1, with an aldehyde of the formula RCHO wherein R is also as defined as above. The ylid is formed from the corresponding phosphonium salt in the usual way by treatment of the phosphonium salt with about one molar equivalent of a strong, organic base, preferably lithium diisopropylamide (LDA) formed in situ by the reaction of n-butyl lithium and diisopropylamine, at low temperature, typically from about

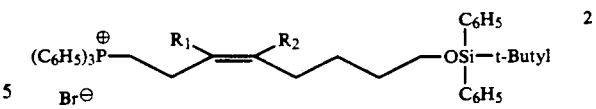

−78° C. to about −25° C., in a suitable solvent, preferably a solvent or solvent combination known to promote the Wittig reaction such as tetrahydrofuran (THF). Hexamethylphosphonictriamide (HMPA), which is known to promote the Wittig reaction by forming a chelate with the lithium counterion, can advantageously be added. The solution of ylid is then allowed to warm slightly to from about −30° C. to about 0° C. and the appropriate aldehyde is added, preferably dropwise, and allowed to react until formation of the desired condensation product of structure 3 is formed. The product can be isolated by quenching the

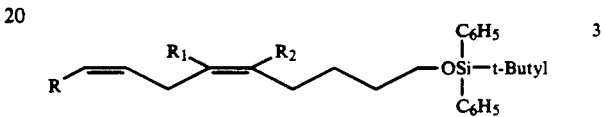

reaction mixture with a saturated, aqueous solution of ammonium chloride and subsequent removal of the organic solvent by evaporation with a rotary evaporator. The mixture is then extracted with diethyl ether to give the isolated product upon evaporation of the ether solvent. The crude product can be purified by, for example, flash chromatography on silicagel eluting with a mixture of hexane and bezene (9:1).

The structure 3 silyl ethers are then converted into the desired fluorinated arachidonic acid derivative of structure 1 wherein X is CO₂H (i.e. the carboxylic acid) via suitable oxidation of the corresponding alcohol of structure 4 formed by treatment of the structure 3 silyl

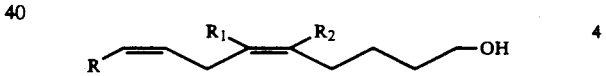

ether with fluoride ion. A solution of the structure 3 silyl ether in THF at room temperature is allowed to react with an excess (1.5 times) of tetra(n-butyl)ammonium fluoride for about 1 to 5 hours and the resulting alcohol is isolated by evaporative solvent removal. Excess Jones Reagent is then added to a cooled (0° C.) acetone solution of the alcohol and the reaction mixture is then allowed to react for about 10 to 30 minutes. Isopropanol is then added to consume excess Jones Reagent and the acetone solvent is removed by evaporation on the rotary evaporator. The residue is then mixed with water and the water mixture is extracted with ethyl acetate. After concentration of the ethyl acetate extracts, flash chromatography on silica gel eluting with a mixture of ethyl acetate and benzene (15:85) results in the isolation of the desired carboxylic acid.

The preparation of the phosphonium bromides, 2, from the dithiolanes 7 is illustrated in Scheme A. Essentially the phosphonium bromides 2 are prepared in the usual manner from the corresponding bromide, 5, by treatment with triphenyl phosphine in refluxing acetonitrile. The derivatives, 6, in any suitable art known procedure. Applicants have prepared the bromo derivatives 5 wherein $R_1$ is a fluoro group by treatment of the alcohol with one equivalent of 1-bromo-N,N-2-trimethylpropenylamine in a cooled (0° C.) methylene chloride solution. The bromo derivatives 5 wherein $R_1$ is hydrogen have been prepared by stepwise conversion of the alcohol, 6, to its mesylate derivative by treatment with methanesulfonic acid chloride in the presence of a proton acceptor such pyridine or triethylamine. Subsequent treatment of the mesyl derivative with a source of bromide ion such as a brominated ion exchange resin, for example, Amberlyst A26, $Br^-$ form, results in the desired bromide 5. The bromination reaction utilizing Amberlyst A26 resin will take from 8 to 24 hours when performed in refluxing benzene. The alcohols 6 are prepared by addition of the 1,3-dithialane derivative 7 to a suspension of one equivalent of trimethyloxonium tetrafluoroborate in methylene chloride. After reaction for about one hour at room temperature, two equivalents of calcium carbonate in aqueous acetone suspension is added and allowed to react overnight. The intermediate aldehyde is isolated and reduced with, for example, sodium borohydride in the usual manner.

phenylsilyl chloride in the presence of a proton acceptor gives the desired 7.

The silylated, dithialane, 7, wherein $R_1$ is a fluoro group and $R_2$ is a hydrogen is prepared from (E) 1-chloro-3-fluoro-4-(2-tetrahydropyranyloxy)-2-butene, 17, as outlined in scheme C. The chloro derivative, 17, is first reacted with N-allyl-N,N',N''-pentamethylphosphoramide in tetrahydrofuran. The intermediate product is isolated and then treated with concentrated hydrochloric acid. Finally the THP (tetrahydropyranyloxy) group is reformed by reaction of the product with dihydropyran (DHP) and catalytic pyridinium paratoluene sulfonate (PPTS) to produce the aldehyde, 16. Reduction in the usual manner with sodium borohydride results in alcohol 15. Treatment of the alcohol with t-butyldiphenylsilyl chloride in the presence of a proton acceptor gives the desired 14. The THP protecting group is then removed by treatment with methanol and tetrabutyl-1,3-diisothiocyanotodistannoxane catalyst to give the alcohol 13. The alcohol is converted to the corresponding bromide, 12, by reaction with 1-bromo-N,N',2-trimethylpropenylamine in methylene chloride solution. The silylated, dithialane, 7, is then produced by reaction of the bromide, 12, with the anion of 1,3-dithiane formed by reaction with n-butyl lithium in cooled (i.e. −30° C.) tetrahydrofuran.

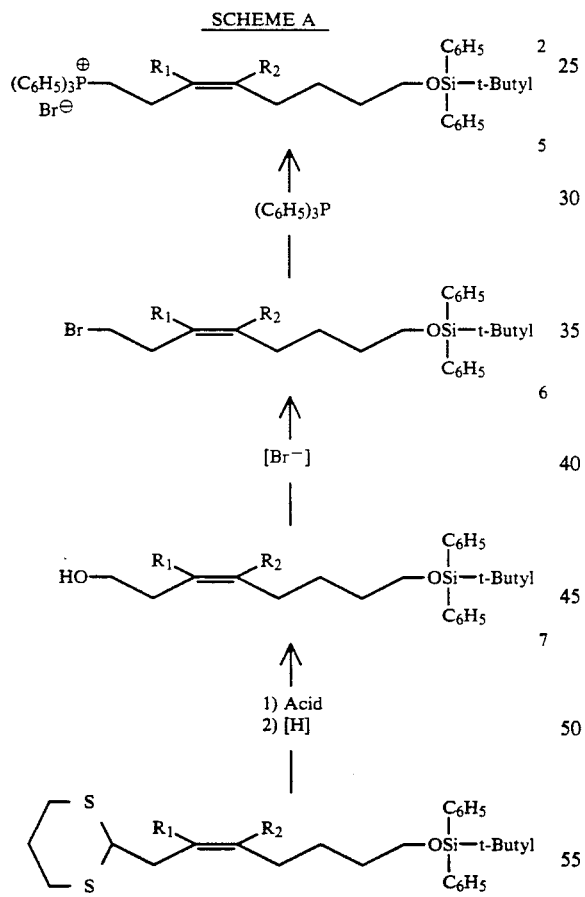

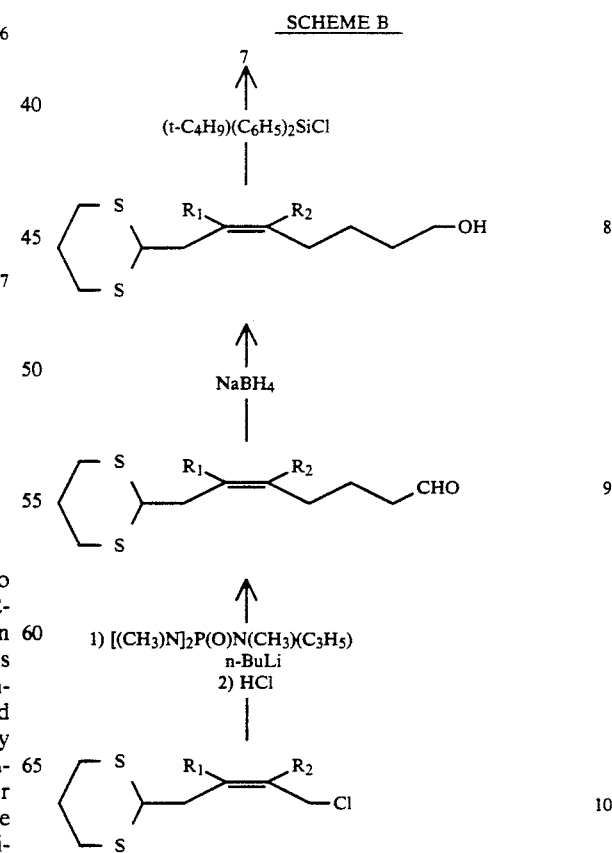

The silylated, dithialanes 7 wherein $R_2$ is a fluoro group are prepared from 3-fluoro-(E)-1-(1,3-dithia-2-cyclohexyl)-4-hydroxy-2-butene, 11, as outlined in scheme B. The hydroxy group of the butene, 11, is converted to a chloro group by reaction with, for example, 1-chloro-N,N,2-trimethylpropene. The chlorinated compound, 10, is transformed into the aldehyde, 9, by reaction with N-allyl-N,N',N''-pentamethylphosphoramide in tetrahydrofuran. Reduction in the usual manner with sodium borohydride results in formation of the alcohol 8. Treatment of the alcohol with t-butyldi- -continued
SCHEME B

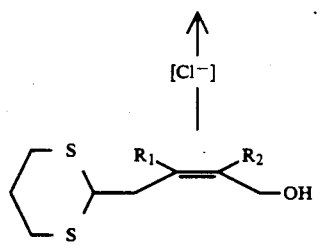

SCHEME C

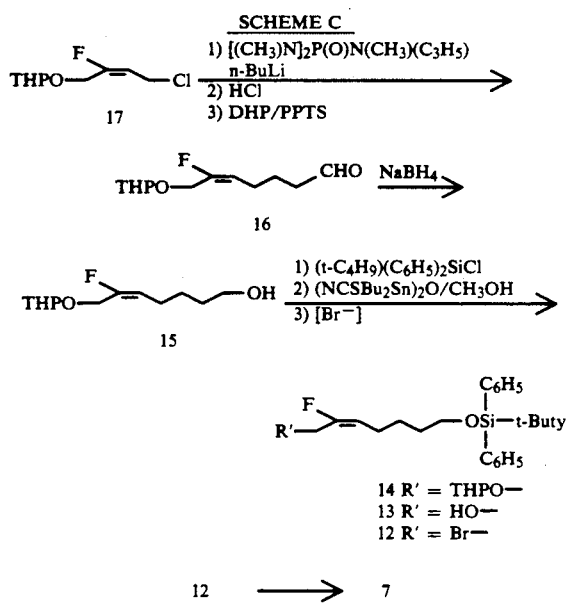

12 ⟶ 7

The hydroxy, dithialane, 11, wherein $R_1$ is a hydrogen and $R_2$ is a fluoro group is prepared from (E)1-chloro-3-fluoro-4-(2-tetrahydropyranyloxy) -2-butene, 17, as outlined in scheme D. The dithialane derivative, 18, is first prepared by reaction of the chloro derivative, 17, with the anion of 1,3-dithiane formed by reaction with n-butyl lithium in cooled tetrahydrofuran.

SCHEME D

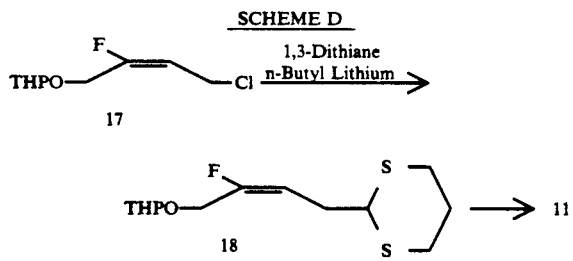

Subsequent removal of the THP protecting group by treatment with methanol and pyridinium paratoluene sulfonate (PPTS) catalyst results in the desired alcohol 11.

The hydroxy, dithialane, 11, wherein $R_1$ and $R_2$ are each a fluoro group are prepared from ethyl 4-bromo-2,3-difluoro-2-buteneoate, 19, by reaction of the anion of 1,3-dithiane formed by reaction of n-butyl lithium in cooled (i.e. -40° C.) tetrahydrofuran to produce the intermediate compound 4-(1,3-dithia-2-cyclohexyl)-2,3-difluoro-2-buteneoate, 20. Subsequent ester group reduction with excess diisobutylaluminun hydride (DIBAL) in THF at about 0° C. gives the desired alcohol 11.

(E) 1-chloro-3-fluoro-4-(2-tetrahydropyranyloxy)-2-butene, 17, is readily prepared from fluoro maleic acid, 21, as illustrated in scheme E. The fluoro maleic acid, 21, is converted to the corresponding dimethylester, 22, by reaction with diazomethane.

SCHEME E

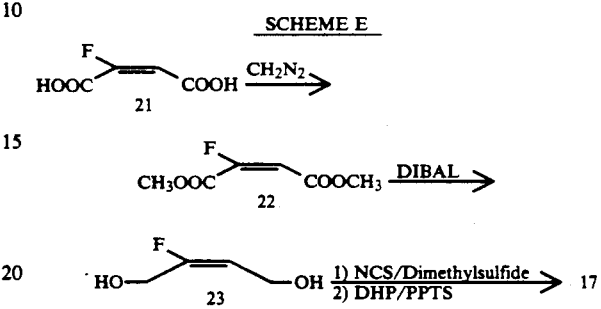

subsequent ester group reduction with excess diisobutylaluminun hydride (DIBAL) in THF at about 0° C. results in formation of the di-alcohol derivative, 23. Selective conversion of the hydroxy group furthest from the fluoro group to a chloro group can be accomplished using a slight (10%) molar excess of N-chlorosuccinimide (NCS) and dimethylsulfide. Protection of the other hydroxy group as the THP derivative can be accomplished in the usual manner by reaction with dihydropyran (DHP) and catalytic pyridinium paratoluene sulfonate (PPTS) results in formation of the desired 17.

The aldehydes of the formula RCHO used to prepare the compounds of this invention can be easily prepared from readily available materials, for example, from the corresponding alcohols by simple oxidation using pyridinium chlorochromate or Collin's reagent in methylene chloride. Many of the alcohols and aldehydes are known. 6-Dodecyn-1-ol is known from J. Chem. Soc., 4363 (1963); (Z)-6-Dodecenal is known from U.S. Pat. No. 4,239,756, granted Dec. 1980; (Z,Z)-3,6-dodecedienal is known from Agric. Biol. Chem., 41, 1481 (1977); and 1-hydroxy-3,6,9-dodecatriyne and (Z,Z,Z)-1-hydroxy-3,6,9dodecatriene are known from Tetrahedron Letters, 22, 4729 (1981). Olefinic alcohols having the (Z) configuration, for example, can be prepared by Nickel boride with ethylene diamine in methanol or ethanol hydrogenation of the corresponding acetylenic alcohols by the procedure of C. A. Brown and V. K. Ahuja, Chemical Comm. 553 (1973).

The optically active aldehyde (24) required to prepared those compounds of formula 1 wherein the R group has the structural formula:

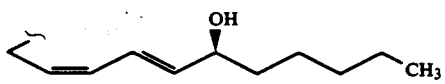

can be prepared from D-arabinose (25) as illustrated in Scheme F. The thioacetal (26) is first prepared from D-arabinose by the procedure described by M. Wong and G. Gray, J. Amer. Chem. Soc. 100, 3548 (1978). The silyloxy aldehyde (27) is then prepared by reaction of the dithioacetal (26) with mercuric oxide and calcium carbonate in refluxing aqueous acetonitrile.

SCHEME F

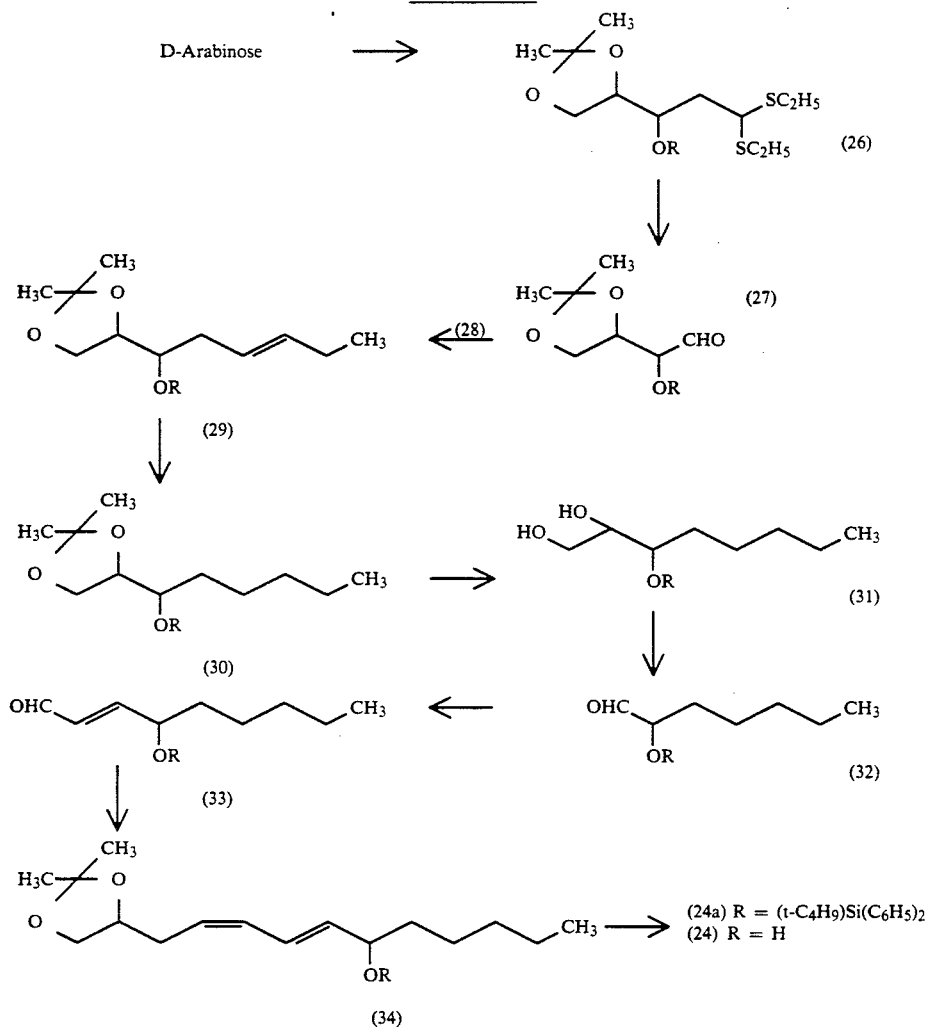

The silyloxy aldehyde (27) is then reacted with the ylid of n-propylbromide and triphenylphosphine (28) formed in the usual manner by reaction with a strong base such as n-butyllithium and potassium t-butoxide in a solvent such as tetahydrofuran. The resulting silyloxyolefin (29) is reduced catalytically with, for example, molecular hydrogen and a palladium on carbon catalyst in acetic acid to form the silyloxy compound (30). The silyloxy compound (30) is converted to the unsaturated aldehyde (33) by the procedure described in G. Just and Z. Wang, Tet. Lett. 26, 2993 (1985) via the diol (31) and the aldehyde (32). Reaction of the unsaturated aldehyde (33) with the ylid of the acetone ketal of 3,4-dihydroxyiodobutane described by P. DeClercy and R. Mijnheen, Bull. Soc. chem. Belg. 87, 495 (1978) in the usual manner results in the diolefinketal (34). Hydrolysis and sodium metaperiodate oxidation in a manner analogous to that described for the conversion of (30) to (32) gives the silyl ether derivative (24a) which upon removal of the silyl group in the usual manner such as by treatment with fluoride ion gives the desired diunsaturated aldehyde (24) wherein the carbon atom bearing the hydroxy group is of the S configuration. Modification of this procedure or chemical modification of the diunsaturated aldehyde can give the other required optically active aldehydes.

The compounds of structure 1 wherein X is other than C(O)OH can be readily prepared from the carboxylic acids by any procedure generally known to those skilled in the art. For example, those compounds of formula 1 wherein X is —C(O)NH$_2$, are prepared from the corresponding compound wherein X is —CO$_2$H by reaction with about 1 molar equivalent of carbonyldiimidazole in an aprotic organic solvent, preferably dichloromethane, for a period of 1 to 7 hours, preferably about 4 hours. Then the product is reacted with a large excess of ammonium hydroxide for from 4 to 64 hours, preferably for about 48 hours. Isolation of the desired compounds of formula 1 wherein X is CONH$_2$ can be by any suitable means known to those in the art.

Alternatively, the compounds of formula 1 wherein X is CONH$_2$ can be prepared by first converting the acid into an activated derivative such as, for example, by reaction of the carboxylic acid with an acyl halide, an anhydride, a mixed anhydride, an alkyl ester, a substituted or unsubstituted phenyl ester, a thioalkyl ester, a thiophenyl ester, an acyl imidazole, and the like. The activated derivative is then reacted with ammonia or aqueous ammonia with or without a suitable water-miscible or immiscible organic solvent, for example, methanol, ethanol, dichloromethane, and the like, so as to produce the amide. The reaction is conducted at from −30° C. to the boiling point of the solvent or solvent mixture used, for from 1 to 96 hours.

Alternatively, the amide can be made by heating together the appropriate compound of formula 1 wherein X is $CO_2H$ and ammonia, or by heating the ammonium salt of a carboxylic acid of formula 1. The reaction is conducted either in the absence of a solvent, or in the presence of a solvent such as, for example, toluene, at a temperature of from 100° C. to 300° C., for from 1 to 12 hours.

Alternatively, the amide can be obtained by hydrolysis of a nitrile derivative (formula 1 wherein X is CN) using either inorganic or organic acids or bases, such as, for example, hydrochloric acid, sulphuric acid, p-toluenesulphonic acid, sodium hydroxide, potassium carbonate, or tetrabutylammonium hydroxide and the like. The reaction is conducted in water optionally containing form 1% to 95% of a cosolvent such as, for example, methanol, acetic acid or diglyme, at a temperature of from 0° C. to the boiling point of the solvent used, for from 1 to 96 hours. Such procedures are well known to those skilled in the art and are described, for example, in *Synthetic Organic Chemistry*, John Wiley and Sons, Publ., New York, 565–590 (1953) and *Compendium of Organic Synthetic Methods*, Vol. 1, Wiley-Interscience, New York, 203–230 (1971).

The compounds of formula 1 wherein X is a 1H-tetrazol-5-yl group can be prepared from the corresponding amide (I wherein X is $CONH_2$) via an intermediate nitrile (I wherein X is CN) derivative. To a solution of an appropriate compound of formula 1 wherein X is $CONH_2$ in a basic organic solvent, preferably pyridine, is added about 1 mole, or equivalent, of an organic sulphonyl halide, preferably p-toluenesulphonyl chloride. The mixture is reacted for 12–48 hours, preferably about 24 hours, and the solution is poured into water. The nitrile is extracted from the aqueous phase with an organic solvent, preferably ethyl ether, and the extract is purified by procedures known in the art.

The isolated nitrile is then reacted with an excess, preferably 3 moles, of an alkali metal azide, preferably sodium azide, and an excess, preferably 3 moles, of an ammonium halide, preferably ammonium chloride, in an aprotic, polar solvent, preferably dimethylformamide, at a temperature of 80° C. to 120° C., preferably 100° C., for 16 to 48 hours, preferably 24 hours optionally in the presence of a Lewis acid such as, for example, boron trifluoride. In this reaction, other sources of azide ion may be used, such as aluminium azide and the azide of tri-n-butyl tin. The product is then isolated by procedures known in the art.

Alternatively, the compounds of formula 1 wherein X is a 1H-tetrazol-5-yl group can be prepared by the reaction between an iminoether derivative of formula 1 wherein $X=C(NH)O(C_1-C_6 alkyl)$ and hydrazoic acid as described in German Patent 521870. The iminoether derivative is obtained by treatment of a nitrile derivative (formula 1 wherein $X=CN$) with a $(C_1-C_6)$ alkanol and a strong acid such as, for example, hydrochloric acid or p-toluenesulphonic acid. The reaction between the iminoether and hydrazoic acid is conducted in the presence of a solvent such as, for example, chloroform or dimethylformamide, at from 0° C. to 120° C., for from 1 to 72 hours. Tetrazole derivatives can also be obtained by the reaction between an amidine derivative of an unsaturated fatty acid, prepared, for example, from the nitrile derivative as described in *Synthetic Organic Chemistry*, John Wiley and Sons, Publ., New York, 635 (1953) and nitrous acid, as described in *Annalen*, 263, 96 (1981), and 208, 91 (1987). The reaction is conducted in water or a mixture of water and a suitable organic solvent such as, for example, methanol or dioxane, at from 0° C. to 100° C., for from 1 to 24 hours.

The esters of compounds of formula I, those wherein X is $C(O)OR^1$ wherein $R^1$ is a straight chain $(C_1-C_6)$ alkyl group can be prepared in the usual manner by esterification of the corresponding carboxylic acid of formula 1 ($X=CO_2H$) by treatment with a solution of hydrogen chloride in the appropriate lower alkanol. Preferably the esters are prepared from the carboxylic acids via the acid chloride derivative. The acid is reacted with a thionyl or phosphoryl halide or phosphorus pentahalide, preferably thionyl chloride, dissolved in an inert organic solvent, preferably benzene, containing a trace of a tertiary organic amide, preferably dimethylformamide. The mixture is reacted for 8–32 hours, preferably for about 16 hours, at from 0° C. to 25° C., then evaporated to dryness. The residue, the acid chloride, is dissolved in an inert organic solvent and the appropriate lower alkanol is added dropwise.

The acylhydroxylamine derivatives, those compounds of formula I wherein X is CONHOH, are prepared in two ways. The acid is either first converted, as described above, into the acid chloride or into a lower alkyl ester, preferably the methyl ester. The acid chloride or the lower alkyl ester is then reacted with an excess of hydroxylamine in an aqueous organic solvent, preferably aqueous methanol, at a pH of between 7 and 10, preferably at about pH 9, for from ¼ to 6 hours, preferably about 1 hour. The acylhydroxylamine product is then isolated by means known in the art.

Acylhydroxylamines can also be prepared by the reaction between hydroxylamine and an activated derivative of an unsaturated fatty acid such as, for example, an acyl halide, an anhydride, a mixed anhydride, an alkyl ester, a substituted or unsubstituted phenyl ester, a thioalkyl ester, a thiophenyl ester, an acyl imidazole, and the like. The reaction is conducted in an aqueous organic or organic solvent such as, for example, methanol, acetonitrile or acetone, at from 0° C. to the reflux temperature of the solvent, for from 1 to 48 hours. Alternately, acylhydroxylamines can be prepared by acid-catalyzed rearrangement of a primary nitro derivative (formula 1, $X=NO_2$) as described in *Chemical Reviews*, 32, 395 (1943). The reaction is conducted in an aqueous organic or organic solvent, such as, for example, methanol, ethanol and dioxan, at from 0° C. to 100° C., for from 1 to 24 hours, in the presence of a strong acid such as, for example, sulphuric acid or hydrochloric acid. Acylhydroxylamine derivatives of unsaturated fatty acids can also be obtained by the oxidation of the oxime derivative of formula 1 wherein $X=CHNOH$ using, for example, hydrogen peroxide as described in *Chemical Reviews*, 33, 225 (1943). The reaction is conducted in a solvent such as methanol or dichloromethane and the like, at from 0° C. to 35° C. for from 1 to 6 hours.

Isolation and purification of the compounds and intermediates described herein can be effected, if desired, by any suitable separation or purification procedure such as, for example, filtration, extraction, crystallization, column chromatography, thin-layer chromatography or thick layer chromatography, or a combination of these procedures. Specific illustrations or suitable separation and isolation procedures can be had by reference to the examples hereinbelow. However, other equivalent separation or isolation proceudres could, of course, also be used.

The pharmaceutically acceptable salts of the compounds of this invention wherein X is $CO_2H$, $C(O)NHOH$ or 1H-tetrazol-5-yl, are prepared by treating the carboxylic acid, acylhydroxylamine or tetrazole compound of formula 1 with at least one molar equivalent of a pharmaceutically acceptable base. Representative pharmaceutically acceptable bases are sodium hydroxide, potassium hydroxide, ammonium hydroxide, calcium hydroxide, metal alkoxides, for example, sodium methoxide, trimethylamine, lysine, caffeine, and the like. The reaction is conducted in water, alone or in combination with an inert, water-miscible organic solvent, or in a suitable organic solvent such as methanol, ethanol, and the like, at a temperature of from about 0° C. to about 100° C., preferably at room temperature. Typical inert, water-miscible organic solvents include methanol, ethanol, or dioxane. The molar ratios of compounds of Formula 1 to base used are chosen to provide the ratio desired for any particular salt.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

The salt products are also isolated by conventional means. For example, the reaction mixtures may be evaporated to dryness, and the salts can be further purified by conventional methods. Salts of the compounds of formula 1 may be interchanged by taking advantage of differential solubilities of the salts, or by treating with the appropriately loaded ion exchange resin.

The amount of a fluorinated arachidonic acid derivative of this invention necessary to control the biosynthesis of or inflammatory states can vary widely according to the particular dosage unit employed, the period of treatment, the age and sex of the patient treated and the nature and extent of the disorder treated. The total amount of the active ingredient to be administered will generally range from about 1 mg/kg to 150 mg/kg and preferably from 3 mg/kg to 25 mg/kg. For example, an average 70 kg human patient will require from about 70 mg to about 10 g of active compound per day. A unit dosage may contain from 25 to 500 mg of active ingredient, and can be taken one or more times per day. The active compound of formula 1 can be administered with a pharmaceutical carrier using conventional dosage unit forms either orally, parenterally, or topically.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intented to assist the break-up and dissolution of the tablet following administration such as potato starch, alginic acid, corn starch, and guar gum, lubricants intented to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intented to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Aerosol or spray compositions containing the compounds of this invention can be applied to the skin or mucous membranes. Such compositions may contain a micronized solid or a solution of a compound of formula 1 and may also contain solvents, buffers, surfactants, perfumes, antimicrobial agents, antioxidants, and propellants. Such compositions may be applied by means of a propellant under pressure or may be applied by means of a compressible plastic spray bottle, a nebulizer, or an atomizer without the use of a gaseous propellant. A preferred aerosol or spray composition is a nasal spray.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, an ocular insert placed in the cul de sac of the eye, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximum number of days during which the carrier is to remains on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compounds of formula 1 may be incorporated in the sustained release carrier in a pure form or may be dissolved in any suitable liquid or solid vehicle, including the polymer of which the sustained release carrier is formed.

EXAMPLE 1

Preparation of 5-Fluoro-5,8,14-Eicosatrienoic Acid

The title compound was prepared from fluoromaleic acid as follows.

1A. Preparation of fluoromaleic acid dimethyl ester

Fluoromaleic acid (37.14 g, 0.277 mole) were esterified in ether at 0° C. by an excess of 0.5M etheral solution of diazomethane until the yellow coloration was stable. Evaporation of the solvent afforded pure diester as an oil (44.71 g, 99.5%). NMR ($H^1$, $CDCl_3$, 60 MHz): 3.78 (s, 3), 3.86 (s. 3). 6.06 (d. $J_{HF}=15.5$ Hz. 1).

1B. Preparation of (E) 1,4-dihydroxy-2-fluoro-2-butene

To a solution of the diester prepared in 1A (20 g, 0.123 mole) in dry tetrahydrofuran (250 ml) cooled to −10° C. was added dropwise under argon a 1.2M diisobutyl aluminium hydride (DIBAL) in hexane (568 ml) while the temperature of the reaction mixture was maintained at 0° C. The mixture was stirred at 0° C. during one hour and during 1 hour at room temperature. The mixture was cooled again to 0° C. and methanol (25 ml) was added dropwise to destroy the excess of DIBAL. Then the aluminium salts were precipitated with an aqueous saturated solution of ammonium chloride added until a filtrable product was obtained. The white-grey solid was filtered and the cake was washed with ethyl acetate containing 10% of methanol. The solvents were evaporated under reduced pressure. The resulting oil was chromatographed on silicagel using pure ethyl acetate as eluent. The diol was obtained as an oil (5.4 g, 41%). NMR ($H^1$, $CD_3OD$, 360 MHz): 4.13 (dd, $J_{HF}=8$ Hz, $J_{HF}=1.5$ Hz, 2), 4.23 (d, $J_{HF}=21$ Hz, 2), 5.43 (dt, $J_{HF}=20$ Hz, $J_{HF}=8$ Hz. 1).

1C. Preparation of (E)-1-chloro-3-fluoro-4-(2-tetrahydropyranyloxy)-2-butene

To a solution of N-chlorosuccinimide (2.76 g, 18 mmoles) in methylene chloride (80 ml) was added to 0° C. dimethylsulfide (1.32 ml, 18 mmoles) and the mixture was stirred for 15 min at 0° C. Then after cooling at −25° C. the diol from 1B (1.74 g, 16.4 mmoles) in methylene chloride (40 ml) was added dropwise. The mixture was stirred successively for 30 min at −25° C., 3 hours at 0° C., and finally 30 min at room temperature. Dihydropyran (3 ml, 32.8 mmoles) and pyridinium para-toluenesulfonate (430 mg, 1.6 mmoles) were added. Thus the mixture was stirred overnight at room temperature. The reaction mixture was washed with water and saturated brine. The organic phase was dried over sodium sulfate. Filtration and flash chromatography on silicagel and elution with a 9:1 mixture of hexane and ethyl acetate afforded the title chloride as an oil (2.69 g, 79%). NMR ($H^1$, $CDCl_3$, 60 MHz): characteristic peaks 4.15 (dd, $J_{HH}=8$ Hz, $J_{HF}=1$ Hz, 2), 4.23 (d, $J_{HF}=20$ Hz, 2), 4.68 (broad s,1), 5.55 (dt, $J_{HH}=8$ Hz $J_{HF}=20$ Hz, 1).

1D. Preparation of (E) 1-(1,3-dithia-2-cyclohexyl)-3-fluoro-4-(2-tetrahydropyranyloxy]-2-butene)

To a solution of 1,3-dithiane (1.55 g, 12.9 mmole) in tetrahydrofuran (60 ml) cooled to −30° C. was added dropwise a 1.32M solution of n-butyllithium in hexane (9.77 ml, 12.9 mmoles), the mixture was stirred at −30° C. for 30 min. Then the mixture was cooled to −40° C. and the chloride prepared in 1C (2.69 g, 12.9 mmoles) in tetrahydrofuran (10 ml) was added dropwise. The reaction was stirred 30 min at −40° C. and 2 hrs at 0° C. The reaction was quenched with saturated aqueous ammonium chloride and the tetrahydrofuran was evaporated under reduced pressure. The residue was diluted with ether and washed with water. The organic layer was dried over sodium sulfate, filtered and concentrated under reduced pressure. Flash chromatography on silicagel and elution with a 8:2 mixture of hexane and ethyl acetate afforded the title dithialane as an oil (3.34 g, 90%). NMR (H$^1$, CDCl$_3$, 60 MHz) characetristic peaks: 4.00 (t, J$_{HH}$=7 Hz, 1), 4.21 (d, J$_{HF}$=20 Hz, 2), 4.7 (broad peak, 1), 5.40 (dt, J$_{HF}$=20 Hz, J$_{HH}$=8 Hz, 1).

1E. Preparation of (E)1-(1,3-dithia-2-cyclohexyl)-3-fluoro-4-ol-2-butene

The tetrahydropyranyl derivative prepared in 1D was dissolved in methanol. Pyridinium para-toluene sulfonate (0.3 g, 1.2 mmoles) was added and the mixture was refluxed for 2.5 hrs. Methanol was evaporated under reduced pressure. The residue was dissolved in ether and washed with water. The organic layer was dried over sodium sulfate, filtered and concentrated under reduced pressure. Flash chromatography on silicagel and elution with a 1:1 mixture of hexane and ethyl acetate afforded the title alcohol as white crystals (2.11 g, 91%). Recrystallization in a mixture of hexane and ether afforded analytically pure samples, m.p.=33.5°–34.5° C. NMR (H$^1$, CDCl$_3$, 60 MHz) characteristic peaks: 4.0 (t, J$_{HH}$=7 Hz, 1), 4.18 (d, J$_{HF}$ 20 Hz, 2), 5.25 (dt, J$_{HF}$=20 Hz, J$_{HH}$=8 Hz, 1). Anal. Calc. for C$_8$H$_{13}$FOS$_2$: C, 46.13; H, 6.29. Found: C, 46.28; H, 6.01).

1F. preparation of (E) 4-chloro-1-(1,3-dithia-2-cyclohexyl)-3-fluoro-2-butene The alcohol prepared in 1E (1.9 g, 9.13 mmoles) was dissolved in dry methylene chloride (70 ml). The mixture was cooled to 0° C. and 1-chloro N,N',2-trimethylpropenylamine (1.23 g, 9.2 mmoles) was added. The mixture was stirred under argon for 15 min. Methylene chloride was evaporated under reduced pressure. Flash chromatography on silicagel and elution with a 9:1 mixture of hexane and ethyl acetate afforded the expected chloride as an oil (1.98 g, 96%). NMR (H$^1$, CDCl$_3$, 60 MHz) characteristic peaks 4.05 (t, J$_{HH}$=7 Hz, 1), 4.13 (d, J$_{HF}$=21 Hz, 2), 5.36 (dt, J$_{HF}$=18 Hz J$_{HH}$=8 Hz, 1).

1G. Preparation of (E) 7-(1,3-dithia-2-Cyclohexyl)-5-fluoro-5-heptenal

To a solution of N-allyl-N, N',N"-pentamethyl phosphoramide (1.5 g, 7.32 mmoles) in tetrahydrofuran (21 ml) cooled to −78° C. was added dropwise n-butyllithium 1.32M in hexane (5.55 ml, 7.32 mmoles). The mixture was stirred under argon at −78° C. for 1 hr. To the resulting red-orange solution, the chloride prepared in 1F in tetrahydrofuran (10 ml) was added dropwise at −78° C. The mixture was stirred for 1 hr at −78° C., then warmed to 0° C. within 2 hrs and stirred 30 min at 0° C. The reaction was quenched with saturated aqueous ammonium chloride and tetrahydrofuran was evaporated under reduced pressure. The resulting oil was diluted with methylene chloride and washed with water. The organic layer was dried over magnesium sulfate. Filtrataion and concentration under reduced pressure afforded an oil. This oil was dissolved in ether (36.5 ml) and was stirred at room temperature during 2 hrs with 2N aqueous solution of hydrochloric acid (36.5 ml). The organic layer was washed twice with water, dried over magnesium sulfate, filtered and concentrated under reduced pressure to afford an oil (1.45 g). Flash chromatography on silicagel and elution with a 25:75 mixture of ethyl acetate and hexane afforded the desired aldehyde (1.014 g, 56%) as an oil. NMR (H$^1$, CDCl$_3$, 60 MHz) characteristic peaks: 4.01 (t, J$_{HH}$=7 Hz, 1), 5.13 (dt, J$_{HF}$=21 Hz, J$_{HH}$=7 Hz, 1), 9.4 (t, J$_{HH}$=1 Hz, 1).

1H. Preparation of (E) 7-(1,3-dithia-2-cyclohexyl)-5-fluoro-5-heptenol

The aldehyde prepared in 1G (0.937 g, 3.77 mmoles) was dissolved in methanol (20 ml) and cooled to 0° C. Sodium borohydride (0.071 g, 1.87 mmoles) was added and the mixture was stirred 30 min. Acetone was added to react with an excess of sodium borohydride and then the reaction mixture was acidified with acetic acid. The solvents were evaporated under reduced pressure. The residue was diluted with ether and washed with water. The organic phase was dried over sodium sulfate, filtered and concentrated under reduced pressure to afford the title alcohol as an oil in a quantitative yield. NMR (H$^1$, CDCl$_3$, 60 MHz) characteristic peaks 4 (t, J$_{HH}$=7 Hz, 1), 5.1 (dt, J$_{HF}$=21 Hz, J$_{HH}$=8 Hz, 1).

1I. Preparation of (E) 1-(t-butyldiphenylsilyoxy)-7-(1,3-dithia-2-cyclohexyl)-5-fluoro-5-heptene To a solution of the alcohol prepared in 1H (2.15 g, 9.26 mmoles) in dry methylene chloride (50 ml) was added triethylamine (2 ml, 14.3 mmoles), t-butyldiphenylchlorosilane (2.65 ml, 10.2 mmoles) and dimethylaminopyridine (45 mg). The mixture was stirred overnight at room temperature. The reaction mixture was washed once with water and then dried over sodium sulfate. Filtration and evaporation under reduced pressure afforded an oil. Flash chromatography on silicagel and elution with a 8:92 mixture of ethyl acetate and hexane afforded the desired silylether as an oil (4.12 g, 94%). NMR (H$^1$, CDCl$_3$, 60 MHz) characteristic peaks 1.06 (s, 9), 3.96 (t, J$_{HH}$=7 Hz, 1), 5.06 (dt, J$_{HF}$=21 Hz J$_{HH}$=8 Hz, 1), 7.23 to 7.80 (m, 10).

1J. Preparation of (E) 8-(t-butyldiphenylsilyloxy)-4-fluoro-3-octenol

To a suspension of trimethyloxonium tetrafluoroborate (0.44 g, 2.97 mmoles) in dry methylene chloride (15 ml) was added at room temperature the dithialane prepared in 1I (1.45 g, 2.97 mmoles) and the mixture was stirred for 1 hr. Then a 9:1 mixture of acetone and water (5 ml) containing calcium carbonate (0.6 g, 5.94 mmoles) was added and the mixture was stirred overnight at room temperature. The precipitate was filtered off and after dilution with saturated brine the mixture was extacted three times with ether. The organic layer was dried over sodium sulfate, filtered and concentrated under reduced pressure to afford an oil. The resulting oil was dissolved in ethanol (10 ml) and sodium borohydride (56 mg, 1.48 mmoles) was added. The mixture was stirred 30 min at 0° C. The excess of sodium boronhydride was reacted with acetone, the mixture was acidified with acetic acid and concentrated under reduced pressure. The residue was taken with water and extracted three times with ether. The organic layer was dried over sodium sulfate, filtered and concentrated under reduced pressure to afford an oil. Flash chromatography on silicagel and elution with a 28:72 mixture of ethyl acetate and hexane afforded the title alcohol as an oil (0.813 g, 74%). NMR (H$^1$, CDCl$_3$, 60 MHz) characteristic peaks: 1.06 (s, 9), 3.4 to 3.8 (m, 4), 5.0 (dt, J$_{HF}$=21 Hz, J$_{HH}$=8 Hz, 7.2 to 7.76 (m, 10).

1K. Preparation of (E) 7-(t-butyldiphenylsilylyloxy)-4-fluoro-1-mesyloxy-3-octene To a solution of the alcohol prepared in 1J (0.813 g, 2.03 mmoles) in dry methylene chloride (10 ml) containing triethylamine (0.43 ml, 3.05 mmoles) cooled to −10° C. was added dropwise mesylchloride (0.2 ml, 2.23 mmoles). The mixture was stirred 15 min at −10° C. then warmed to room temperature. The reaction mixture was washed three times with water. The organic layer was dried over sodium sulfate, filtered and concentrated under reduced pressure to afford the expected mesylate as an oil which was used without purification. NMR (H$^1$, CDCl$_3$, 60 MHz) characteristic peaks: 1.06 (s, 9), 2.09 (s, 3), 4.1 (t, J$_{HH}$=7, Hz, 2], 4.96 (dt, J$_{HF}$=20 Hz, J$_{HH}$=8 Hz, 1), 7.16 to 7.83 (m, 10).

1L. Preparation of (E) 1-bromo-8-(t-butyldiphenylsilyloxy)-4-fluoro-3-octene To a solution of the mesylate prepared in 1K (0.985, 2.03 mmoles) in benzene (50 ml) was added dry Amberlyst-A -26 Br form (4.2 g) and the mixture was refluxed overnight under stirring. Filtration and evaporation under reduced pressure afforded an oil (0.86 g). Flash chromatography on silicagel and elution with a 98:2 mixture of hexane and ethyl acetate afforded the title bromide as an oil (0.825 g). NMR (H$^1$, CDCl$_3$, 60 MHz) characteristic peaks: 1.06 (s, 9,), 3.25 (t, J$_{HH}$=7 Hz, 2), 3.66 (m, 2), 5.0 (dt, J$_{HF}$=21 Hz, J$_{HH}$=8 Hz, 1), 7.2 to 7.7 (m, 10).

1M. Preparation of (E) 8-(t-butyldiphenylsilyloxy)-4-fluoro-3-octenyltriphenyl phosphonium bromide A mixture of the bromide prepared in 1L (0.825 g, 1.78 mmoles) and triphenylphosphine (0.61 g, 2.31 mmoles) in dry acetonitrile (10 ml) were refluxed for 48 hrs. Evaporation of the solvent under reduced pressure, flash chromatography on silicagel and elution with a 9:1 mixture of methylene chloride and methanol afforded the expected phosphonium bromide as a foam (0.982 g, 81%).

1N. Preparation of (E) 1-[t-butyldiphenylsilyloxy) -5-fluoro-5,8,14-eicosatriene To a solution of diisopropylamine (0.15 ml, 1.08 mmoles) in tetrahydrofuran (10 ml) cooled to −78° C. was added dropwise n-butyllithium 1.6M in hexane solution (0.68 ml, 1.08 mmoles). The mixture was warmed to −10° C. and then cooled again to −78° C. The phosphonium bromide prepared in 1M (0.787 g, 1.08 mmoles) in tetrahydrofuran (4 ml) was added dropwise and the mixture was stirred 30 min at −78° C. Hexamethylphosphonictriamide (0.5 ml) was added and the reaction mixture was warmed to −30° C. (Z) 3-dodecenal (0.187 g, 0.97 mmole) in tetrahydrofuran (2 ml) was added dropwise and the mixture was stirred 2 hrs at −30° C. and 30 min at 0° C. Saturated aqueous solution of ammonium chloride was added and tetrahydrofuran was evaporated under reduced pressure. The residue was taken up with water and extracted three times with ether. The organic layer was washed twice with water and dried over sodium sulfate. Filtration and evaporation of the solvent afforded an oil. Flash chromatography on silicagel and elution with a 9:1 mixture of hexane and benzene afforded the expected triene (298 mg, 56%). NMR (H$^1$, CDCl$_3$, 60 MHz) characteristic peaks: 3.65 (m, 2), 4.66 to 5.60 (m, 5), 7.16 to 7.86 (m, 10).

1O. Preparation of 5-fluoro-5,8,14-eicosatrienol

To a solution of the silylether prepared in 1N (237 mg, 0.43 mmole) in tetrahydrofuran (5 ml) was added tetra-n-butylammonium fluoride trihydrate (205 mg, 0.65 mmole). The mixture was stirred at room temperature for 2 hr. The solvent was evaporated under reduced pressure. The residue was dissolved in methylene chloride, washed with water and dried over sodium sulfate. Filtration and concentration under reduced pressure afforded an oil. Flash chromatography on silicagel and elution with a 15:95 mixture of ethyl-acetate and benzene afforded the expected alcohol as an oil (119 mg, 88%). NMR (H$^1$, CDCl$_3$, 360 MHz) characteristic peaks: 2.32 (dm, J$_{HF}$=21.6 Hz, 2), 2.72 (t, J$_{HH}$=7 HZ, 2), 3.73 (m, 2), 5.09 (dt, J$_{HF}$=21.6 Hz, J$_{HH}$=8 Hz, 1), 5.39 (m, 4).

1P. Preparation of 5-fluoro-5,8,14-eicosatrienoic acid

To a solution of the alcohol prepared in 1O (119 mg, 0.38 mmoles) in acetone (3 ml) cooled to 0° C. was added dropwise 2.67M Jones reagent over 15 min until the orange color was stable. The mixture was stirred 15 min at 0° C. The excess of Jones reagent was reacted with isopropanol. The acetone was evaporated under reduced pressure without heating. The residue was taken up with water and extracted three times with ethyl acetate. The organic layer was dried over sodium sulfate, filtered and concentrated under reduced pressure to leave an oil (90 mg). Flash chromatography on silicagel and elution with a 15:85 mixture of ethyl acetate and benzene gave pure acid (55 mg, 45%). NMR (H$^1$, CDCl$_3$, 360 MHz): 0.87 (t, J$_{HH}$=6.92 Hz, 3), 1.245 to 1.45 (m, 20), 1.86 (quint, J$_{HH}$=7.25 Hz, 2), 2.01 (m, 6), 2.16 (dt, J$_{HF}$=22 Hz, J$_{HH}$=7.28 Hz, 2), 2.4 (t, J$_{HH}$=7.41 Hz, 2), 2.64 (t, J$_{HH}$=7.52 Hz, 2), 5.06 (dt, J$_{HF}$=21.5 Hz, J$_{HH}$=8 Hz, 1), 5.24 to 5.44 (m, 4).

EXAMPLE 2

Preparation of 6-Fluoro-5,8,14-Eocpsatrienoic Acid

The title compound was prepared from (E) 1-chloro-3-fluoro-4-(2-tetrahydropyroxylaxy)-2-butene.

2A. Preparation of (E) 6-fluoro-7-(2-tetrahydropyranyloxy)-5-heptenal

To a solution of N-allyl-N,N'N"-pentamethylphosphoramide (2.50 g, 11.99 mmoles) in tetrahydrofuran (30 ml) cooled to −78° C. was added dropwise n-butyllithium 1.55M in hexane (7.74 ml, 11.93 mmoles). The mixture was stirred under argon at −78° C. for 1 hr. To the resulting red-orange solution the chloride prepared in 1C in tetrahydrofuran (15 ml) was added dropwise at −78° C. The mixture was stirred for 1 hr at −78° C., then warmed up to 0° C. within 2 hrs and stirred 1 hr at 0° C. The reaction was quenched with saturated aqueous ammonium chloride and the tetrahydrofuran was evaporated under reduced pressure. The resulting oil was diluted with methylene chloride and washed with water. The organic layer was dried over magnesium sulfate. Filtration and concentration under reduced pressure afforded an oil. This oil was dissolved in ether (60 ml) and was stirred at room temperature for 2 hrs with a 2N aqueous solution of hydrochloric acid (60 ml). The organic layer was washed twice with water, dried over magnesium sulfate, filtered and concentrated under reduced pressure to afford an oil (2.10 g). The NMR of the crude mixture showed that the THP has been mostly cleaved. To a solution of the crude oil in methylene chloride (100 ml) was added dihydropyran (2.1 ml) and pyridinium paratoluene sulfonate (0.236 g) and the mixture was stirred overnight at room temperature. The reaction mixture was washed with water. The organic layer was dried over sodium sulfate. Filtration and concentration under reduced pressure afforded an oil (3 g). Flash chromatography on silicagel and elution with a 25:75 mixture of ethyl acetate and hexane afforded the aldehyde (1.74 g, 64%) as an oil. NMR (H$^1$, CDCl$_3$, 360 MHz) characteristic peaks: 4.18 (AB part of an ABX system, $J_{H_AH_B}$=13 Hz, $J_{H_AF}$=20.5 Hz, $J_{H_BF}$=24.6 Hz, 2), 1), 9.77 (t, $J_{HH}$=1.5 Hz, 1).

2B. Preparation of (E) 6-fluoro-7,12-tetrahydropyranyloxy)-5-heptanol

The aldehyde prepared in 2A (1.34 g, 7.56 mmoles) was dissolved in methanol (20 ml) and cooled to 0° C. Sodium borohydride (0.143 g, 3.78 mmoles) was added and the mixture was stirred 30 min. Acetone was added to react with the excess of sodium borohydride. The solvents were evaporated under reduced pressure. The residue was diluted with ether and washed with water. The organic phase was dried over sodium sulfate, filtered and concentrated under reduced pressure to afford pure alcohol as an oil (1.66 g) which was used to the next step without purification.

2C. Preparation of (E) 1-(t-butyldiphenylsilyloxy)-6-fluoro-7-(2-tetrahydropyranyloxy)-5-heptene To a solution of the alcohol prepared in 2B (1.66 g, 7.15 mmoles) in dry methylene chloride (50 ml) was added triethylamine (1.7 ml, 11.34 mmoles), t-butyldiphenylchlorosilane (1.7 ml, 8.31 mmoles) and dimethylaminopyridine (40 mg). The mixture was stirred overnight at room temperature. The reaction mixture was washed once with water and then dried over sodium sulfate. Filtration and evaporation under reduced pressure afforded an oil. Flash chromatography on silicagel and elution with a 10:90 mixture of ethyl acetate and hexane afforded the silylether as an oil (2.87 g).

2D. Preparation of (E) 1-(t-butyldiphenylsilyloxy)-6-fluoro-5-heptene-7-ol

The tetrahydropyranyl derivative prepared in 2C (2.26 g, 4.8 mmoles) was dissolved in methanol. Tetrabutyl-1,3-diisothiocyanatodistannoxane (30 mg) was added and the mixture was refluxed for 24 hrs. Methanol was evaporated under reduced pressure. The residue was dissolved in ether and washed with water. The organic layer was dried over sodium sulfate, filtered and concentrated under reduced pressure. Flash chromatography on silicagel and elution with a 2:8 mixture of hexane and ethyl acetate afforded the alcohol as an oil (1.65 g, 92%).

2E. Preparation of (E) 7-bromo-1-(t-butyldiphenylsilyloxy)-6-fluoro-5-heptene The alcohol prepared in 2D (1.1 g, 2.85 mmoles) was dissolved in dry methylene chloride (20 ml). The mixture was cooled to 0° C. and 1-bromo,N,N',2-trimethylpropenylamine (0.51 g, 2.85 mmoles) was added. The mixture was stirred under argon for 15 min. Methylene chloride was evaporated under reduced pressure. Flash chromatography on silicagel and elution with a 95:5 mixture of hexane and ethyl acetate afforded the expected bromide as an oil (1.24 g, 98%). NMR (H$^1$, CDCl$_3$, 60 MHz) characteristic peaks: 1.05 (s, 9), 3.65 (m, 2), 3.91 (d, $J_{HF}$=22 Hz, 2), 5.23 (dt, $J_{HF}$=19 Hz, $J_{HH}$=7.5 Hz, 1), 7.26 to 7.78 (m, 10).

2F. Preparation of (E) 1-(t-butyldiphenylsilyloxy)-7-(1,3-dithia-2-cyclohexyl)-6-fluoro-5-heptene To a solution of dithialane (0.365 g, 3.04 mmole) in tetrahydrofuran (50 ml) cooled to −30° C. was added dropwise a 1.5M solution of n-butyllithium in hexane (2 ml, 3 mmoles) and the mixture was stirred at −30° C. for 30 min. in 2E (1.24 g, 2.76 mmoles) in tetrahydrofuran (10 ml) was added dropwise. The reaction was stirred 30 min at −40° C. and 2 hrs at 0° C. and then quenched with saturated aqueous ammonium chloride and the tetrahydrofuran was evaporated under reduced pressure. The residue was diluted with ether and washed with water. The organic layer was dried over sodium sulfate, filtered and concentrated under reduced pressure. Flash chromatography on silicagel and elution with a 95:5 mixture of hexane and ethyl acetate afforded the desired dithialane as an oil (0.524 g, 40%). NMR (H$^1$, CDCl$_3$, 60 MHz) characteristic peaks: 1.03 (s, 9), 3.61 (m, 2), 4.23 (t, $J_{HH}$=7.5 Hz, 1), 5.3 (dt, $J_{HF}$=21 Hz, $J_{HH}$=7.5 Hz, 1), 7.16 to 7.83 (m, 10).

2G. Preparations of (E) 8-(t-butyldiphenylsilyloxy)-3-fluoro-3-octenol

To a solution of the dithialane prepared in 2F (0.424 g, 0.86 mmoles) in dry methylene chloride (4 ml) was added at room temperature trimethyloxonium tetrafluoroborate (0.125 g, 0.86 mmoles) and the mixture was stirred for 1 hr. Then a 9:1 mixture of acetone and water (2 ml) containing calcium carbonate (0.172 g, 1.72 mmoles) was added and the mixture was stirred overnight at room temperature. The precipitate was filtered off and after dilution with saturated brine the mixture was extracted three times with ether. The organic layer was dried over sodium sulfate, filtered and concentrated under reduced pressure to afford an oil. The resulting oil was dissolved in ethanol (5 ml) and sodium borohydride (19 mg, 0.50 mmoles) was added. The mixture was stirred for 30 min at 0° C. The excess of sodium borohydride was treated with acetone, the mixture was acidified with acetic acid and concentrated under reduced pressure. The residue was taken up with water and extracted three times with ether. The organic layer was dried over sodium sulfate, filtered and concentrated under reduced pressure to afford an oil. Flash chromatography on silicagel and elution with a 25:75 mixture of ethyl acetate and hexane afforded the desired alcohol as an oil (0.168 g, 49%).

2H. Preparation of (E) 1-bromo-8-t-butyldiphenylsilyloxy)-3-fluoro-3-octene

The alcohol prepared in 2G (0.168 g, 0.42 mmoles) was dissolved in dry methylene chloride (5 ml). The mixture was cooled to 0° C. and 1-bromo N,N',2-trimethylpropenylamine (75 mg, 0.42 mmoles) was added. The mixture was stirred under argon for 30 min. The methylene chloride was evaporated under reduced pressure. Flash chromatography on silicagel and elution with a 95:5 mixture of hexane and ethyl acetate afforded the expected bromide as an oil (0.112 g, 57%). NMR (H$^1$, CDCl$_3$, 60 MHz) characteristic peaks: 1.05 (s, 9), 2.66 (dt, $J_{HF}$=21 Hz, $J_{HH}$=7 Hz, 2), 3.40 (t, $J_{HH}$=7 Hz, 2), 3.61 (m, 2), 5.1 (dt, $J_{HF}$=22 Hz, $J_{HH}$=7.5 Hz, 1), 7.16 to 7.76 (m, 10).

2I. Preparation of (E) 8-(t-butyldiphenylsilyloxy)-3-fluoro-3-octenyl triphenyl phosphonium bromide A mixture of the bromide prepared in 2H (0.112 g, 0.24 mmoles) and triphenylphosphine (0.083 g, 0.31 mmoles) in dry acetonitrile (5 ml) were refluxed for 48 hrs. Evaporation of the solvent under reduced pressure, flash of methylene chloride and methanol afforded the expected phosphonium bromide as a foam (0.097 g, 56%). NMR ($H^1$, $CDCl_3$, 90 MHz) characteristic peaks: 1.0 (s, 9), 3.6 (t, $J_{HH}=6Hz$), 3.76 to 4.16 (m, 2), 4.96 (dt, $J_{HF}=21$ Hz, $J_{HH}=7.5$ Hz, 1), 7.23 to 8.05 (m, 25).

2J. Preparation of (E) 1-(t-butyldiphenylsilyloxy)-5-fluoro-5,8,14-eicosatriene To a solution of diisopropylamine (0.02 ml, 0.14 mmoles) in tetrahydrofuran (2 ml) cooled to $-78°$ C. was added dropwise n-butyllithium 1.5M in hexane solution (0.09 ml, 0.13 mmoles). The mixture was warmed to $-10°$ C. and then cooled again to $-78°$ C. The phosphonium bromide prepared in 2I (0.093 g, 0.12 mmoles) in tetrahydrofuran (1 ml) was added dropwise and the mixture was stirred 45 min at $-78°$ C. Hexamethylphosphonictriamide (0.25 ml) was added and the reaction mixture was warmed to $-25°$ C. (Z) 3-dodecenal (0.022 g, 0.12 mmole) in tetrahydrofuran (1 ml) was added dropwise and the mixture was stirred 30 min at $-25°$ C. and 1 hr at $0°$ C. Saturated aqueous solution of ammonium chloride was added and tetrahydrofuran was evaporated under reduced pressure. The residue was taken up with water and extracted three times with ether. The organic layer was washed twice with water and dried over sodium sulfate. Filtration and evaporation of the solvent afforded an oil. Flash chromatography on silicagel and elution with a 99:1 mixture of hexane and ethyl acetate afforded the expected triene (58 mg, 81%). NMR ($H^1$, $CDCl_3$, 90 MHz) characteristic peaks: 2.95 (dd, $J_{HF}=22$ Hz, $J_{HH}=6$ Hz, 2), 3.66 (t, $J_{HH}=6$ Hz, 2), 5 (dt, $J_{HF}=21$ Hz, $J_{HH}=7.5$ Hz, 1), 5.23 to 5.66 (m, 4), 7.3 to 7.85 (m, 10).

2K. Preparation of 6-fluoro-5,8,14-eicosatrienol

To a solution of the silylether (58 mg, 0.1 mmole) in tetrahydrofuran (2 ml) was added tetra-n-butylammonium fluoride trihydrate (50 mg, 0.15 mmole). The mixture was stirred at room temperature for 2 hr. The solvent was evaporated under reduced pressure. The residue was dissolved in methylene chloride, washed with water and dried over sodium sulfate. Filtration and concentration under reduced pressure afforded an oil. Flash chromatography on silicagel and elution with a 2:8 mixture of ethyl acetate and hexane afforded the expected alcohol as an oil (21 mg, 68%).

2L. Preparation of 6-fluoro-5,8,14-eicosatrienoic acid

To a solution of the alcohol prepared in 2K (21 mg, 0.067 mmoles) in acetone (2 ml) cooled to $0°$ C. was added dropwise 2.67M Jones reagent until the organe color was stable. The mixture was stirred 15 min at $0°$ C. The excess of Jones reagent was reacted with isopropanol. The acetone was evaporated under reduced pressure without heating. The residue was taken with water and extracted three times with ethyl acetate. The organic layer was dried over sodium sulfate, filtered and concentrated under reduced pressure to leave an oil (20 mg). Flash chromatography on silicagel and elution with a 25:75 mixture of ethyl acetate and hexane gave pure title acid (14 mg, 64%). NMR ($H^1$, $CDCl_3$, 360 MHz): 0.89 (t, $J_{HH}\sim7$ Hz, 3), 1.21 to 1.45 (m, 10), 1.51 (quint, $J_{HH}\sim7$ Hz, 2), 1.98 to 2.12 (m, 8), 2.37 (t, $J_{HH}\sim7$ Hz, 2), 2.96 (dd, $J_{HF}=23$ Hz, $J_{HH}=6.8$ Hz, 2), 4.98 (dt, $J_{HH}=21.2Hz$, $J_{HH}=7.9$ Hz, ]), 5.3 to 5.5 (m, 4).

We claim:

1. A fluorinated arachidonic acid derivative of the formula

wherein $R_1$ is a fluoro group and $R_2$ is hydrogen or $R_1$ and $R_2$ are each independently a fluoro group;

X is a C(O)OR' group wherein R' is hydrogen, a straight chain ($C_1$-$C_6$)alkyl group, or X is a group of the formula —C(O)OCH$_2$CH(OR")CH$_2$(OR''') wherein R" is an acyl residue or a long chain, fatty acid and wherein R''' is hydrogen or an acyl residue of a long chain, fatty acid, X is a —C(O)NH$_2$ or —C(O)NH(OH) group, or X is a 1H-tetrazol-5-yl group; and R is a group of one of the structural formulae

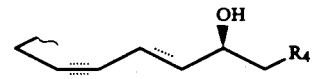

wherein $R_3$ is a hydrogen or a straight chain ($C_1$-$C_4$)alkyl and $R_4$ is hydrogen or a straight chain ($C_1$-$C_6$)alkyl and wherein the dotted line indicates an optional double or triple bond
as well as where X is (C(O)OR' and R' is hydrogen, or the pharmaceutically acceptable salt thereof.

2. A fluorinated arachidonic acid derivative of claim 1 wherein $R_1$ and $R_2$ are both fluorine.

3. A fluorinated arachidonic acid derivative of one of claims 1, or 2 wherein X is a $CO_2H$ group.

4. A fluorinated arachidonic acid derivative of one of claims 1 or 2 wherein X is a group of the formula —C(O)OCH$_2$CH(OR")CH$_2$(OR''') wherein R" is an acyl residue of a long chain, fatty acid and wherein R''' is hydrogen or an acyl residue of a long chain, fatty acid.

5. A fluorinated arachidonic acid derivative of one of claims 1 or 2 wherein R is a group of the structural formula

wherein $R_3$ is hydrogen or a straight chain ($C_1$-$C_4$)alkyl and wherein the dotted line indicates an optional double or triple bond.

6. A fluorinated arachidonic acid derivative of claim 5 wherein $R_3$ is an ethyl group.

7. A fluorinated arachidonic acid derivative of one of claims 1 or 2 wherein R is a group of the structural formula

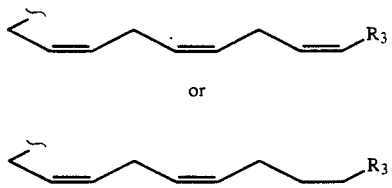

wherein $R_3$ is hydrogen or a straight chain $(C_1-C_4)$alkyl.

8. A fluorinated arachidonic acid derivative of claim 7 wherein $R_3$ is an ethyl group.

9. A fluorinated arachidonic acid derivative of claim 1 wherein $R_1$ is fluorine and $R_2$ is hydrogen.

10. A method of inhibiting 5-lipoxygenase in a patient in need thereof which comprises administering to the patient an amount effective to inhibit 5-lipoxygenase of a fluorinated arachidonic acid derivative of the formula

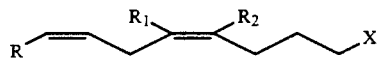

wherein $R_1$ is a fluoro group and $R_2$ is hydrogen or $R_1$ and $R_2$ are each independently a fluoro group;

X is a C(O)OR' group wherein R' is hydrogen, a straight chain $(C_1-C_6)$ alkyl group, or X is a group of the formula —C(O)OCH$_2$CH(OR'')CH$_2$(OR''') wherein R'' is an acyl residue or a long chain, fatty acid and wherein R''' is hydrogen or an acyl residue of a long chain, fatty acid, X is a —C(O)NH$_2$ or —C(O)NH(OH) group, or X is a 1H-tetrazol-5-yl group; and R is a group of one of the structural formulae

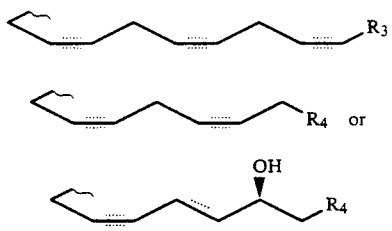

wherein $R_3$ is hydrogen or a straight chain $(C_1-C_4)$alkyl and $R_4$ is hydrogen or a straight chain $(C_1-C_6)$alkyl and wherein the dotted line indicates an optional double or triple bond
as well as where X is (C(O)OR' and R' is hydrogen, or the pharmaceutically acceptable salt thereof.

11. A method of claim 10 wherein $R_1$ is fluorine.

12. A method of claim 10 wherein $R_1$ and $R_2$ are both fluorine.

13. A method of one of claims 10, 11 or 12 wherein X is a CO$_2$H group.

14. A method of one of claims 10, 11, or 12 wherein X is a group of the formula —C(O)OCH$_2$CH(OR'')CH$_2$(OR''') wherein R'' is an acyl residue of a long chain, fatty acid and wherein R''' is hydrogen or an acyl residue of a long chain, fatty acid.

15. A method of claims 10, 11, or 12 wherein R is a group of the structural formula

wherein $R_3$ is hydrogen or a straight chain $(C_1-C_4)$ alkyl and wherein the dotted line indicates an optional double or triple bond.

16. A method of claim 15 wherein $R_3$ is an ethyl group.

17. A method of one of claims 10, 11 or 12 wherein R is a group of the structural formula

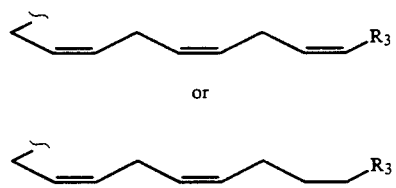

wherein $R_3$ is hydrogen or a straight chain $(C_1-C_4)$alkyl.

18. A method of claim 17 wherein $R_3$ is an ethyl group.

19. A method of treating asthma in a patient in need thereof which comprises administering to the patient an amount effective to treat asthma of a fluorinated arachidonic acid derivative of the formula

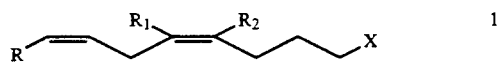

wherein $R_1$ is a fluoro group and $R_2$ is hydrogen or $R_1$ and $R_2$ are each independently a fluoro group;

X is a C(O)OR' group wherein R' is hydrogen, a straight chain $(C_1-C_6)$ alkyl group, or X is a group of the formula —C(O)OCH$_2$CH(OR'')CH$_2$(OR''') wherein R'' is an acyl residue or a long chain, fatty acid and wherein R''' is hydrogen or an acyl residue of a long chain, fatty acid.

X is a —C(O)NH$_2$ or —C(O)NH(OH) group, or

X is a 1H-tetrazol-5-yl group; and

R is a group of one of the structural formulae

wherein $R_3$ is hydrogen or a straight chain $(C_1-C_4)$alkyl and $R_4$ is hydrogen or a straight chain $(C_1-C_6)$alkyl and wherein the dotted line indicates an optional double or triple bond
as well as where X is (C(O)OR' and R' is hydrogen, or the pharmaceutically acceptable salt thereof.

20. A method of claim 19 wherein $R_1$ is fluorine.

21. A method of claim 19 wherein $R_1$ and $R_2$ are both fluorine.

22. A method of one of claims 19, 20 or 21 wherein X is a CO$_2$H group.

23. A method of one of claims 19, 20 or 21 wherein X is a group of the formula —C(O)OCH$_2$CH(OR″)CH$_2$(OR‴) wherein R′ is an acyl residue of a long chain, fatty acid and wherein R‴ is hydrogen or an acyl residue of a long chain, fatty acid.

24. A method of one of claims 19, 20, or 21 wherein R is a group of the structural formula

wherein R$_3$ is hydrogen or a straight chain (C$_1$–C$_4$)alkyl and wherein the dotted line indicates an optional double or triple bond.

25. A method of claim 24 wherein R$_3$ is an ethyl group.

26. A method of one of claims 19, 20 or 21 wherein R is a group of the structural formula

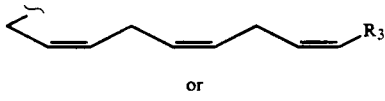

or

wherein R$_3$ is hydrogen or a straight chain (C$_1$–C$_4$)alkyl.

27. A method of claim 26 wherein R$_3$ is an ethyl group.

* * * * *

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

At Column 4, line 32, the patent reads "bezene" and should read --benzene--.

At Column 4, lines 66 and 67, the patent reads "The derivatives, 6, in any suitable art known procedure." and should read --The bromides, 5, can be prepared from the corresponding alcohol derivatives, 6, in any suitable art known procedure.--.

At Column 7, line 45, the patent reads "n-butyl lithium in cooled tetrahydrofuran" and should should read -- n-butyl lithium in cooled (i.e. -30°C) tetrahydrofuran--.

At Column 8, line 1, the patent reads "diisobutylaluminun" and should read --diisobutylaluminum--.

At Column 8, line 23, the patent reads "subsequent" and should read --Subsequent--.

At Column 8, line 46, the patent reads "3,6,9dodecatriene" and should read --3,6,9-dodecatriyne--.

At Column 10, line 53, the patent reads "4 to 64" and should read --24 to 64--.

At Column 13, line 1, the patent reads "proceudres" and should read --procedures--.

At Column 13, lines 51 and 52, the patent reads "biosynthesis of or inflammatory states..." and should read --biosynthesis of leukotrienes prophylactically or to treat existing allergic or inflammatory states...--.

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

At Column 16, lines 22 and 23, the patent reads "$J_{HF}$ = 8 Hz," and should read --$J_{HH}$ = 8 Hz,--.

At Column 16, line 25, the patent reads "$J_{HF}$ = 8 Hz. 1)." and should read --$J_{HH}$ = 8Hz, 1).

At Column 16, line 27, the patent reads "tetrahydropyranvloxy" and should read --tetrahydropyranyloxy--.

At Column 17, line 2, the patent reads "characetristic" and should read --characteristic--.

At Column 18, line 62, the patent reads "8 Hz, 7.2 to 7.76 (m, 10)." and should read --8 Hz, 1), 7.2 to 7.6 (m, 10).--

At Column 20, line 36, the patent reads "Eocpsatrienoic" and should read --Eicosatrienoic--.

At Column 21, line 9, the patent reads "$J_{HBF}$ = 24.6 Hz, 2), 1), 9.77 (t, $J_{HH}$ = 1.5 Hz, 1)." and should read "$J_{HBF}$ = 24.6 Hz, 2), 4.68 (t, $J_{HH}$ = 3.4 Hz, 1), 5.25 (dt, $J_{HH}$ = 8.2 Hz, $J_{HF}$ = 20.4 Hz, 1), 9.77 (t, $J_{HH}$ = 1.5 Hz, 1).--.

At Column 22, line 9, the patent reads "30 min. in 2E" and should read --30 min. Then the mixture was cooled to -40°C and the bromide prepared in 2E--.

At Column 24, line 4, the patent reads "7.9 Hz, ])," and should read --7.9 Hz, 1),--.

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

COLUMNS 24 and 25

--CLAIMS SHOULD READ--

1. A fluorinated arachidonic acid derivative of the formula

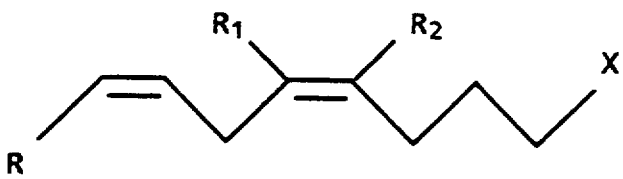

1 wherein $R_1$ is a fluoro group and $R_2$ is a hydrogen or $R_1$ and $R_2$ are
each independently a fluoro group;
X is a C(O)OR' group wherein R' is a hydrogen, a straight chain ($C_1$-$C_6$)alkyl group, or
X is a group of the formula
$-C(O)OCH_2CH(OR'')CH_2(OR''')$ wherein R'' is an acyl residue or a long chain, fatty acid and
wherein R''' is a hydrogen or an acyl residue of a long chain, fatty acid,
X is a 1H-tetrazol-5-yl group; and
X is a 1H-tetrazol-5-yl group; and
R is a group of one of the structural formulae

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

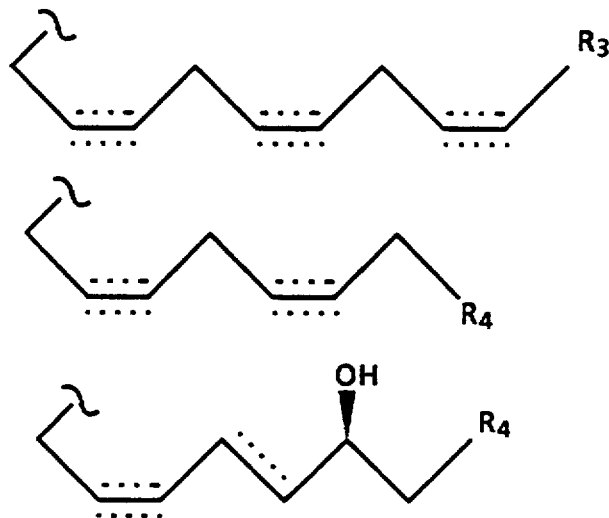

wherein $R_3$ is hydrogen or a straight chain $(C_1-C_4)$alkyl and $R_4$ is hydrogen or a straight chain $(C_1-C_6)$alkyl and wherein the dotted line indicates an optional double or triple bond as well as where X is C(O)OR' and R' is hydrogen, or the pharmaceutically acceptable salt thereof.

2. A fluorinated arachidonic acid derivative of claim 1 wherein $R_1$ is fluorine and $R_2$ is hydrogen.

3. A fluorinated arachidonic acid derivative of claim 1 wherein $R_1$ and $R_2$ are both fluorine.

4. A fluorinated arachidonic acid derivative of one of claims 1, 2 or 3 wherein X is a $CO_2H$ group.

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

5. A fluorinated arachidonic acid derivative of one of claims 1, 2 or 3 wherein X is a group of the formula $-C(O)OCH_2CH(OR'')CH_2(OR''')$ wherein $R''$ is an acyl residue of a long chain, fatty acid and wherein $R'''$ is hydrogen or an acyl residue of a long chain, fatty acid.

6. A fluorinated arachidonic acid derivative of one of claims 1, 2 or 3 wherein R is a group of the structural formula

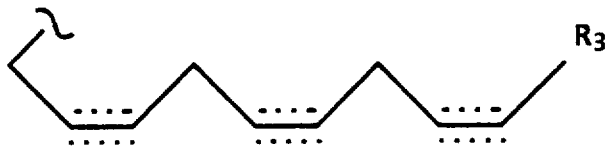

wherein $R_3$ is hydrogen or a straight chain $(C_1-C_4)$alkyl and wherein the dotted line indicates an optional double or triple bond.

7. A fluorinated arachidonic acid derivative of claim 6 wherein $R_3$ is an ethyl group.

8. A fluorinated arachidonic acid derivative of one of claims 1, 2 or 3 wherein R is a group of the structural formula

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

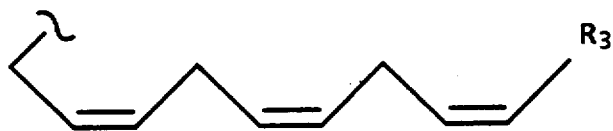

or

wherein $R_3$ is hydrogen or a straight chain $(C_1-C_4)$alkyl.

9. A fluorinated arachidonic acid derivative of claim 8 wherein $R_3$ is an ethyl group.

10. A method inhibiting 5-lipoxygenase in a patient in need thereof which comprises administering to the patient an amount effective to inhibit 5-lipoxygenase of a fluorinated arachiodonic acid derivative of the formula

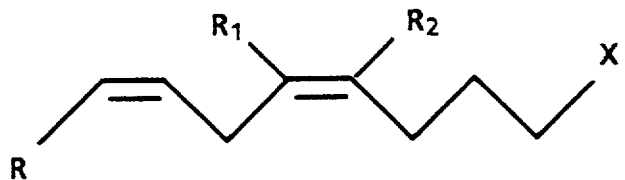

1

UNITED STATES PATENT AND TRADEMARK OFFICE
CERTIFICATE OF CORRECTION

PATENT NO. : 5,145,861
DATED : September 8, 1992
INVENTOR(S) : Jean B. Ducep and Jean-Francois Nave It is certified that error appears in the above-indentified patent and that said Letters Patent is hereby corrected as shown below:

wherein $R_1$ is a fluoro group and $R_2$ is hydrogen or $R_1$ and $R_2$ are each independently a fluoro group;
- X    is a C(O)OR' group wherein R' is hydrogen, a straight chain $(C_1-C_6)$alkyl group, or
- X    is a group of the formula $-C(O)OCH_2CH(OR'')CH_2(OR''')$ wherein R'' is an acyl residue or a long chain, fatty acid and wherein R''' is hydrogen or an acyl residue of a long chain, fatty acid,
- X    is a $-C(O)NH_2$ or $-C(O)NH(OH)$ group, or
- X    is a 1H-tetrazol-5-yl group; and
- R    is a group of one of the structural formulae

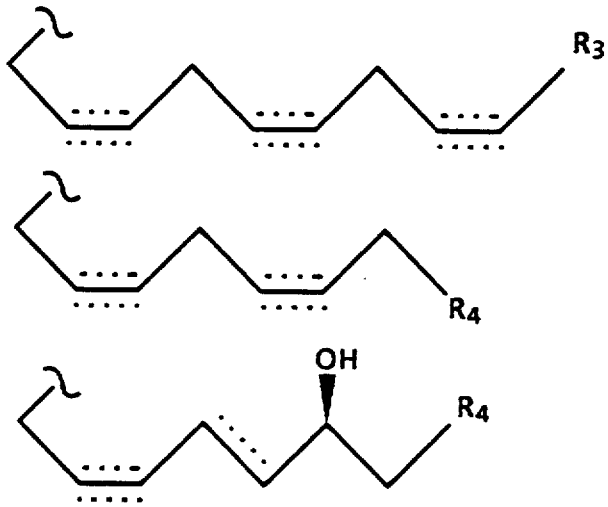

UNITED STATES PATENT AND TRADEMARK OFFICE
CERTIFICATE OF CORRECTION

PATENT NO. : 5,145,861

DATED : September 8, 1992

INVENTOR(S) : Jean B. Ducep and Jean-Francois Nave

It is certified that error appears in the above-indentified patent and that said Letters Patent is hereby corrected as shown below:

```
wherein R₃ is hydrogen or a straight chain (C₁-C₄)alkyl and
        R₄ is hydrogen or a straight chain (C₁-C₆)alkyl and
           wherein the dotted line indicates an optional double or
           triple bond
as well as where X is C(O)OR' and R' is hydrogen or the
pharmaceutically acceptable salt thereof.
```

Signed and Sealed this

Sixth Day of December, 1994

Attest:

BRUCE LEHMAN

*Attesting Officer*  *Commissioner of Patents and Trademarks*